US00PP08887P

United States Patent [19]

Cook

[11] Patent Number: Plant 8,887

[45] Date of Patent: Sep. 13, 1994

[54] *GARDENIA JASMINOIDES* VAR. STAR BRIGHT

[75] Inventor: Allyn A. Cook, 109 SW. 101 Ct., Gainesville, Fla. 32607

[73] Assignee: Allyn A. Cook, Gainesville, Fla.

[21] Appl. No.: 130,139

[22] Filed: Nov. 8, 1993

[51] Int. Cl.[5] ..... A01H 5/00

[52] U.S. Cl. ..... Plt./67.6

[58] Field of Search ..... Plt. 67.6

[56] References Cited

PUBLICATIONS

Huxley, A., et al "*Gardenia*" *The New R.H.S. Dictionary of Gardening* vol. 2 1992, the MacMillan Press, Ltd., N.Y., pp. 366, 367.

*Primary Examiner*—James R. Feyrer

[57] ABSTRACT

A new and novel seedling *Gardenia jasminoides* plant, named 'Star Bright' is disclosed and is particularly characterized by its large, single flowers of pure white petal color. Petals have elongated claws, which are covered at their articulation with the corolla tube, by normally strongly reflexed golden-yellow, elongated anthers which assume an adpressed position over the basal petal connections. Petals and anthers are inferior to the lobed stigma which is of a slightly lighter color than that of the anthers. The classic, simple, single white flowers stand out conspicuously over the lush, deep green leaves. The plant is a multi-stemmed rounded shrub of medium canopy density which attains a height and span of two or more meters when growing under conditions to which it is adapted.

3 Drawing Sheets

BACKGROUND AND FIELD OF THE INVENTION

In the course of gardening activities in my home garden near the west side of Gainesville, Fla., about 1980, I harvested a seed pod resulting from the Open Pollination of a dwarf Gardenia (*Gardenia jasminoides* Ellis). From seed removed from the pod of the parent plant, six plants were obtained. All of the seedlings were later moved to another location in the same general area, and two were observed to bloom in 1991. In the evaluation of the plants as they grew and developed, it became apparent that one plant, the selection which is the subject of this description, strongly departed from the characteristics of the seed parent, and combined a number of characteristics which made it a highly desirable candidate for use as a landscape appointment. The seed parent plant, which is no longer available, was a dwarf, double flowered plant, with small, white, fragrant flowers and small leaves. Flowers were about two to four centimeters in size and leaves were lanceolate and about four centimeters long and one centimeter wide.

The plant here described forms an attractive shrub which can attain a height and spread of about two meters, or more, has much larger foliage than the parent plant, and forms a attractive shrub. This plant has a canopy of medium density, composed of large attractive, deep green leaves. Flowers are attractive, large, single, normally have six, but occasionally seven or eight, white petals, and an alluring fragrance. Upon realizing the novelty and desirable characteristics of this plant, I immediately took steps to preserve and multiply it. With the recognition that this plant has numerous advantageous traits, has very large, perfect flowers, is fertile, and has accessible reproductive organs, it became my intention to employ it as a parent plant in a planned breeding program. With the above noted traits, after further culture and observation, it was noticed that this plant also exhibits resistance to insect infestations, which is a particularly advantageous characteristic in culture of this plant where it is adapted to grow in the open. Finally, this plant is uniquely suited for landscape use due to its vigor and characteristic ability to produce an abundance of large, fragrant, strikingly attractive star-shaped flowers which contrast pleasingly with the lush, deep green foliage. In recognizing the unusual characteristics of this plant, I have denominated it 'Star Bright'.

I have asexually reproduced this plant by rooting softwood cuttings in my home garden in the area the west side of Gainesville, Fla. With the observation of approximately fifty clones of this plant, I have concluded that the distinguishing characteristics of clonal offspring are substantially identical to those of the original specimen and conclude that the plant is stable.

SUMMARY OF THE INVENTION

The plant of this invention is a unique, shrub Gardenia which forms an attractive, large specimen plant. A combination of notable characteristics which distinguish it from its seed parent as well as other Gardenia plants is as follows:

'Star Bright' has the ability to form a large, vigorous specimen with an attractive, rounded form.

The plant of this disclosure forms a canopy of medium density, and has leaves of large size combined with high durability against weather and insects.

This plant presents large, attractive, single, white flowers which have a pleasant fragrance similar to but differing slightly in character from that of other members of the species of the seed parent.

Petals are pure white, spatulate, and long, usually six in number, and give the flowers the appearance of a star against the contrasting green leaves.

The flowers are produced in large numbers, and are of unusually large scale, simple in character, and pleasantly contrasting over the lush, deep green foliage.

Flower are perfect and fertile. Due to their scale, the flower parts, lend themselves to the use of this plant as either a pollen or seed parent in planned breeding programs.

The flowers of this plant have six anthers that alternate with the petals and become recurved away from the pistillate complex. This exposes abundant pollen as the flower opens, and subtilely defines the lower petal portions above the corolla.

These and other characteristics identify the unusually attractive plant which is depicted in the various showings of the drawing.

BRIEF DESCRIPTION OF THE PHOTOGRAPHS OF THE DRAWING

In the drawing, the top photograph of a first sheet depicts, in perspective, the white, single flower at close range, over the contrasting deep green, healthy foliage. The bottom photograph shows a mature specimen of the plant of this disclosure, with two yard sticks placed end-to-end to give an idea of the height and spread of the plant of this disclosure.

A second sheet of drawing depicts, at the top, the top surfaces of leaves of, from left to right, progressive maturity from recently formed to fully mature. In the bottom photograph, the under-surfaces of the leaves are shown. These photographs show the smooth margin, shape, venation, surface aspect, and color of leaves. The ruler at the right reflects the size of the pictured leaves.

A third sheet, top photo, shows a branch terminal, stripped of leaves, and illustrates the internode length, color of previous and current seasons bark, the terminal bud, axillary buds, and three flower buds. The two bottom photos show, on the left, the flower in plan view to depict petals, anthers, and pistil complex; and, on the right, a bisected specimen of the flower to show the receptacle, sepals, corolla tube, stamens and pistil.

DETAILED BOTANICAL DESCRIPTION OF THE PLANT

Growth Habit

This plant's growth habit is similar to that of the genus in general, but differs primarily in vigor and scale which greatly exceed that of most domestic members of the genus. The plant will grow to a shrub of about two meters height and spread, or more, in the space of about eight years time. It forms a rounded to mounded specimen with a canopy of medium density when planted as a foundation plant in a partially shaded location in the area of west Gainesville, Fla. Canopy density can be varied by pruning, planting in a location of greater light exposure, and variations in amount and analysis of fertilizer applied. Internodes can reach nine centimeters.

Multiple main stems of moderate thickness are formed; no central leader dominates. Lateral branches extend from the main stems at angles approaching 45 degrees, and are strong. Secondary branches are slender. Branches may sweep with advancing length, but may be headed back by pruning to maintain the plant in a desired size, shape and canopy density. Habit might be best described as weakly ascending to weakly spreading.

Bark

Mature bark is grey and substantially smooth. Current season's bark is a deep green which is essentially the same color of the leaves. Terminal bud scales are retained through at least two growth flushes, leaving a mark to indicate growth flushes. Mature bark color and character are not seen to particularly distinguish this plant.

Foliage

Leaves are positioned opposite and/or in a whorl of three in relative positions of 60 degrees. Leaves are generally elliptic to lanceolate, with acuminate tips. Bases are acuminate. Margins are smooth; leaves are essentially symmetrical. Venation is palmate. At the top surface, veins are slightly depressed, and are conspicuous when viewed from the bottom surface by their lighter green color and exserted position. Top surfaces are deep green and semi-glabrous, not atypical of the genus. Bottom surfaces are matt and of only slightly lighter green, again, not unusual for the genus. Top surfaces are slightly undulated, with mounding between veins, mostly between the midrib and the margins. Leaves are leathery and have short petioles. This plant bears persistent, interpetiolate, membranous, tubular stipules immediately above the stem nodes. These structures might be referred to as terminal bud scales referred to above. Mature leavs range in size from about 9 to about 15 centimeters in length. Width of leaves typically is less than half the length.

Bud and Flower Structures

Buds are formed near the terminals of the branches, usually within the last four nodes, and presented on short, sturdy pedicels. The calyx cup is characterized by five to eight, usually six, flattened wings to six centimeters in length, that extend to the pedicel ridges. Flowers are nearly sessile, terminal or axillary. The flowers attain a size to 11.8 centimeters in diameter. They first appear in late April in northern Florida. Flowers are characterized by six, but range from five to seven or eight, pure white, broadly spatulate petals. Petal dimensions range from 3–3.5×4.5–5 centimeters and are borne on a basal corolla tube which may attain a length of 3.5 centimeters and has a diameter of 5 millimeters. Each of six sessile, versatile anthers have a length of 8–11 mm and are normally, but not always, alternate with petals and are inserted in the throat of the corolla tube. Anthers are inferior to stigmas, and are of a contrasting golden color. Following anthesis, which occurs before flower opening, pollen from each anther adheres to the outer, membranous tissue of the sections of the stigma. The narrow style (1–2 mm diameter ×3.5 cm length) extends through the corolla tube to an inferior ovary, as shown. Stigmas are in the form of two or more enlarged lobes of golden-yellow hue which may splay or separate with advancing maturity. The style is white and slightly tapered from the stigma to the ovary.

Fruit and Seed

Roughly spherical fruits attain a diameter to 1.5 centimeters and require nearly eight months to mature. Fruits mature turning from green and hard when immature to bright orange and soft when mature. Sepals which are slightly longer than th corolla tube, and of a green substantially like that of the leaves, are retained through the development of the fruit. Seeds are flattened and are about 12 mm in diameter. The color of the seeds is cream to light brown.

Further Observations

Young but mature stem cuttings than include at least two nodes root readily when placed in soil and kept moist.

This plant is characterized by the production of abundant, large "single" flowers typical with six white, broadly spatulate petals which lie in a single plane. Production of gold to yellow pollen is abundant. The plant is fertile. These traits make the disclosed plant a candidate as either the pollen parent or the seed parent in controlled breeding programs, to develop new varieties. The described plant has also exhibited resistance to the insect infestations which bother other Gardenia plants in the Northern Florida location of origin. This is a desirable trait for landscape planting for which the plant is uniquely suited by its vigor and its production of an abundance of large, fragrant flowers.

I claim:

1. A new and novel Gardenia plant (*Gardenia jasminoides*) as described and illustrated, named 'Star Bright'.

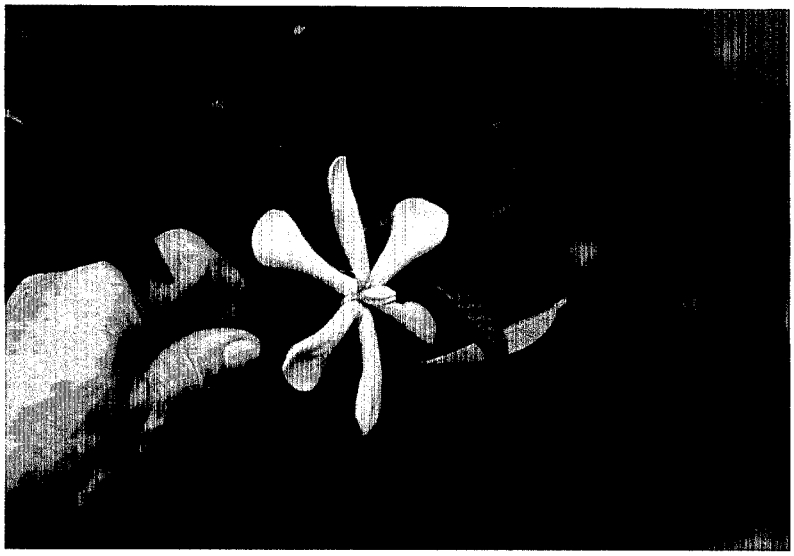
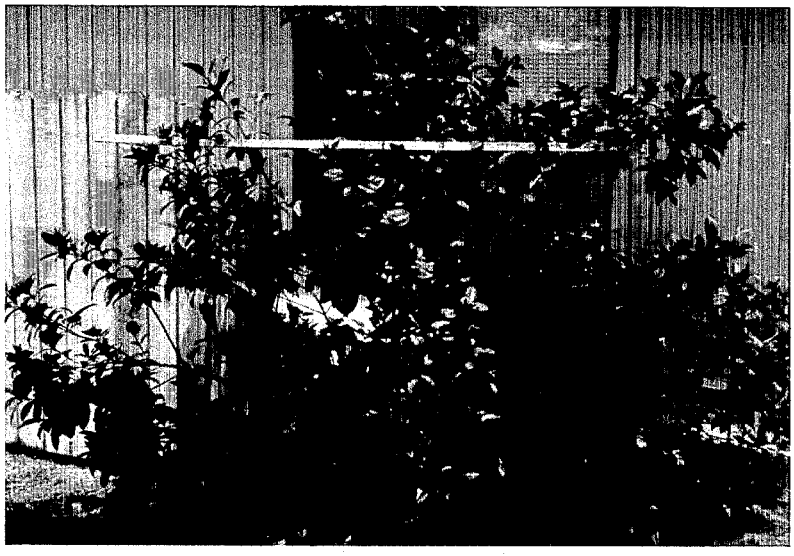

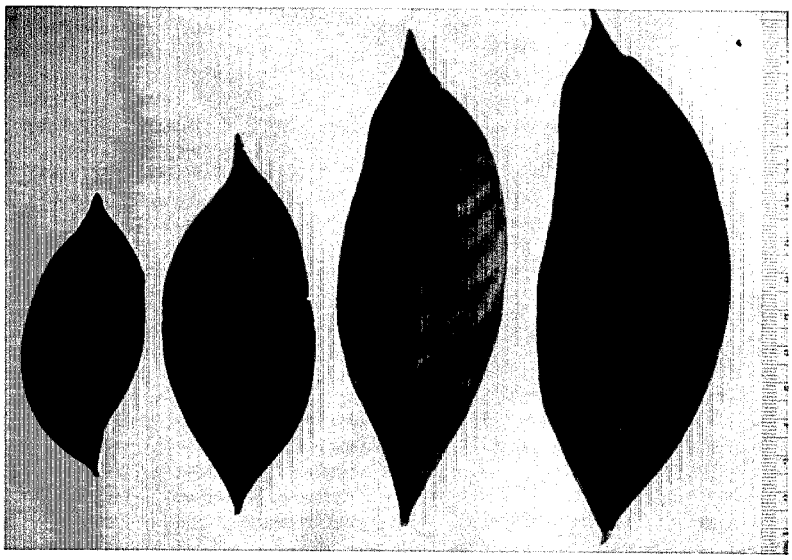
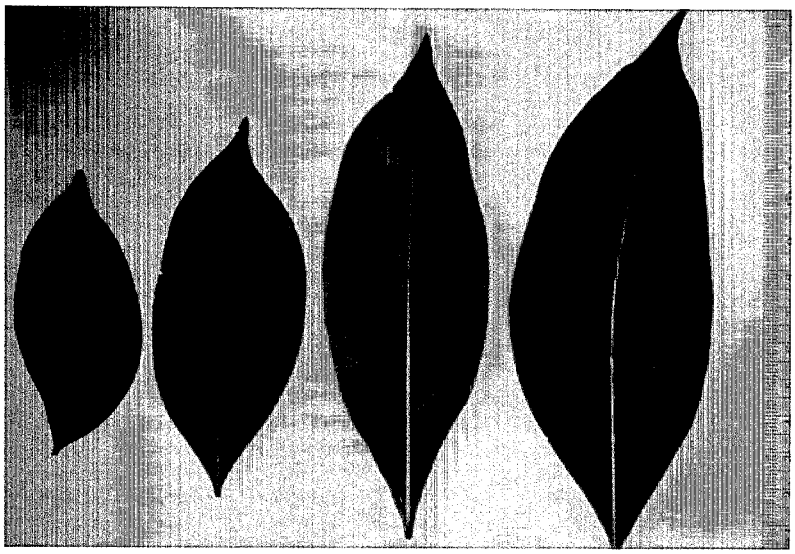

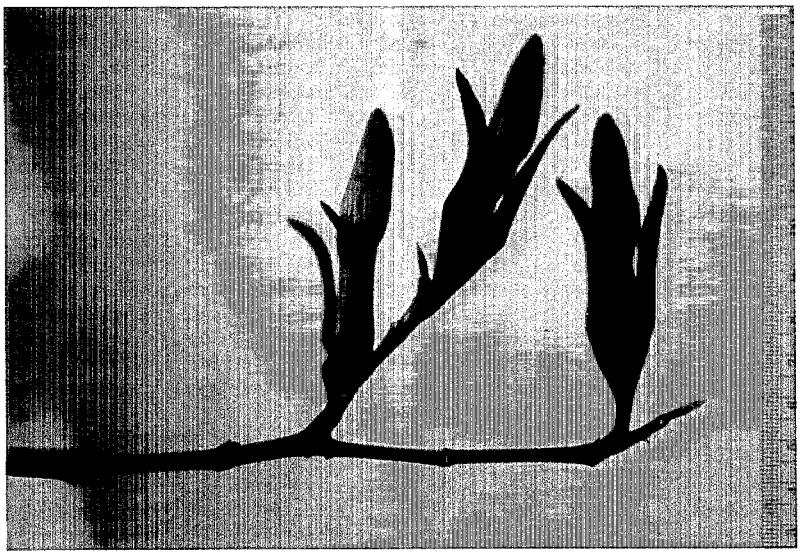
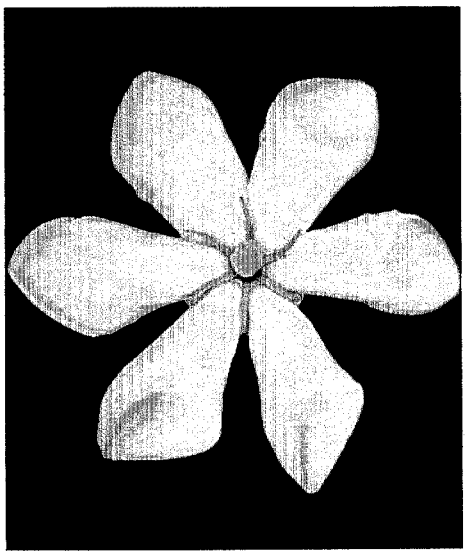
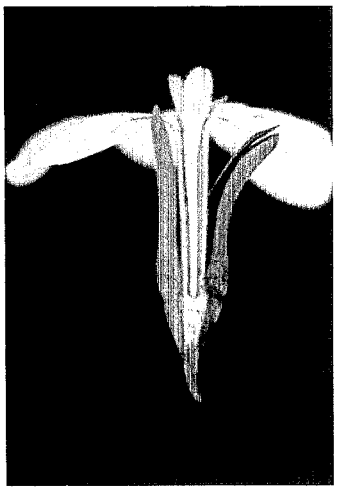

* * * * *